(12) United States Patent
Hugg

(10) Patent No.: US 10,631,819 B2
(45) Date of Patent: Apr. 28, 2020

(54) MOLECULAR BREAST IMAGING METHOD

(71) Applicant: KROMEK GROUP, PLC

(72) Inventor: James William Hugg, Mars, PA (US)

(73) Assignee: KROMEK GROUP, PLC, Sedgefield, County Durham (GB)

( * ) Notice: Subject to any disclaimer, the term of this patent is extended or adjusted under 35 U.S.C. 154(b) by 0 days.

(21) Appl. No.: 16/030,468

(22) Filed: Jul. 9, 2018

(65) Prior Publication Data

US 2018/0310897 A1 Nov. 1, 2018

Related U.S. Application Data

(62) Division of application No. 15/096,075, filed on Apr. 11, 2016.

(60) Provisional application No. 62/145,790, filed on Apr. 10, 2015.

(51) Int. Cl.
| | | |
|---|---|---|
| *A61B 8/08* | (2006.01) | |
| *A61B 6/04* | (2006.01) | |
| *A61B 6/12* | (2006.01) | |
| *A61B 6/03* | (2006.01) | |
| *A61B 6/06* | (2006.01) | |
| *A61B 6/00* | (2006.01) | |
| *G21K 1/02* | (2006.01) | |

(52) U.S. Cl.
CPC ............ *A61B 8/0825* (2013.01); *A61B 6/037* (2013.01); *A61B 6/0414* (2013.01); *A61B 6/06* (2013.01); *A61B 6/12* (2013.01); *A61B 6/4266* (2013.01); *A61B 6/4429* (2013.01); *A61B 6/502* (2013.01); *A61B 6/4417* (2013.01); *A61B 8/0841* (2013.01); *G21K 1/025* (2013.01)

(58) Field of Classification Search
CPC ......... A61B 6/502; A61B 8/0825; A61B 6/12; A61B 6/037; A61B 6/4429; A61B 6/4266; A61B 6/0414; A61B 6/4417; A61B 8/0841; G21K 1/025
See application file for complete search history.

(56) References Cited

U.S. PATENT DOCUMENTS

| | | | |
|---|---|---|---|
| 4,419,585 | A | 12/1983 | Strauss et al. |
| 5,519,221 | A | 5/1996 | Weinberg |
| 5,534,701 | A * | 7/1996 | Pierfitte ............... A61B 6/4441 250/363.04 |
| 6,377,838 | B1 | 4/2002 | Iwanczyk et al. |
| 8,115,171 | B2 | 2/2012 | Blevis |
| 8,217,357 | B2 | 7/2012 | Stein et al. |
| 8,541,748 | B2 | 9/2013 | Blevis |
| 8,592,772 | B2 | 11/2013 | Stein et al. |
| 8,610,076 | B2 | 12/2013 | Blevis |
| 8,853,635 | B2 | 10/2014 | O'Connor |
| 8,886,293 | B2 | 11/2014 | O'Connor et al. |

(Continued)

*Primary Examiner* — Amanda Lauritzen Moher
*Assistant Examiner* — Chao Sheng
(74) *Attorney, Agent, or Firm* — Ference & Associates LLC

(57) ABSTRACT

A system and method for molecular breast imaging (MBI) using pixelated gamma cameras provide easier patient positioning and biopsy access using compression paddles and movable gamma cameras. The paddles and cameras can be curved to better conform to the breast shape. A variable angle slant-hole collimator is provided to assist in stereotactic imaging for biopsy guidance. Methods for performing an MBI screening or diagnostic examination and guiding a biopsy with stereotactic MBI are provided.

10 Claims, 10 Drawing Sheets

MBI flow chart.

(56) References Cited

U.S. PATENT DOCUMENTS

| | | |
|---|---|---|
| 9,060,732 B2 | 6/2015 | O'Connor |
| 9,711,251 B2 | 7/2017 | Lee et al. |
| 2005/0063509 A1* | 3/2005 | Defreitas ............. A61B 6/0414 |
| | | 378/37 |
| 2008/0242979 A1* | 10/2008 | Fisher .................. A61B 6/4233 |
| | | 600/427 |
| 2010/0261997 A1* | 10/2010 | Ren ........................ A61B 6/037 |
| | | 600/424 |
| 2010/0329419 A1* | 12/2010 | Blevis .................... A61B 6/037 |
| | | 378/37 |
| 2012/0130234 A1* | 5/2012 | O'Connor ............ A61B 6/0414 |
| | | 600/427 |
| 2012/0148016 A1* | 6/2012 | Blevis ...................... A61B 6/06 |
| | | 378/37 |
| 2014/0093035 A1 | 4/2014 | Beekman |
| 2014/0110592 A1 | 4/2014 | Nelson et al. |
| 2014/0303483 A1* | 10/2014 | Schellenberg ..... A61B 10/0041 |
| | | 600/411 |
| 2016/0007944 A1 | 1/2016 | O'Connor |

\* cited by examiner

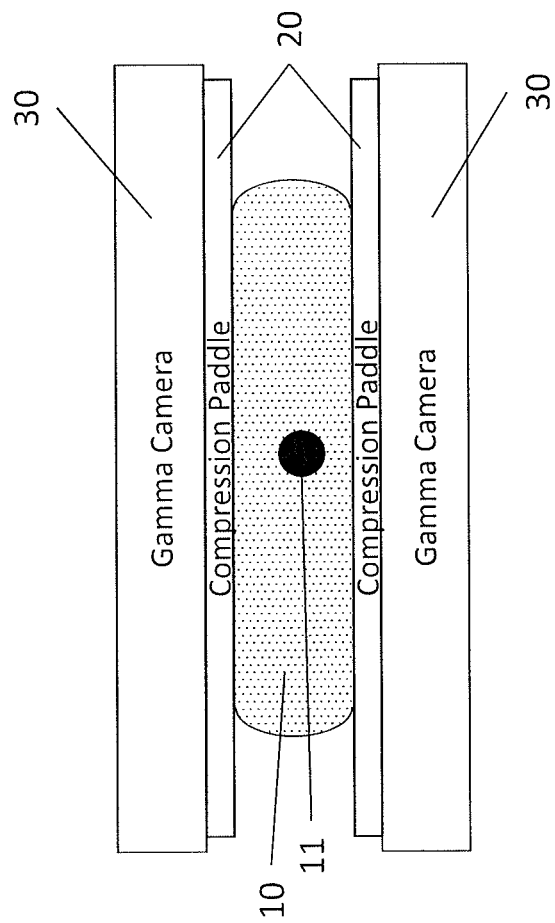
Figure 3. Gantry (nipple) view

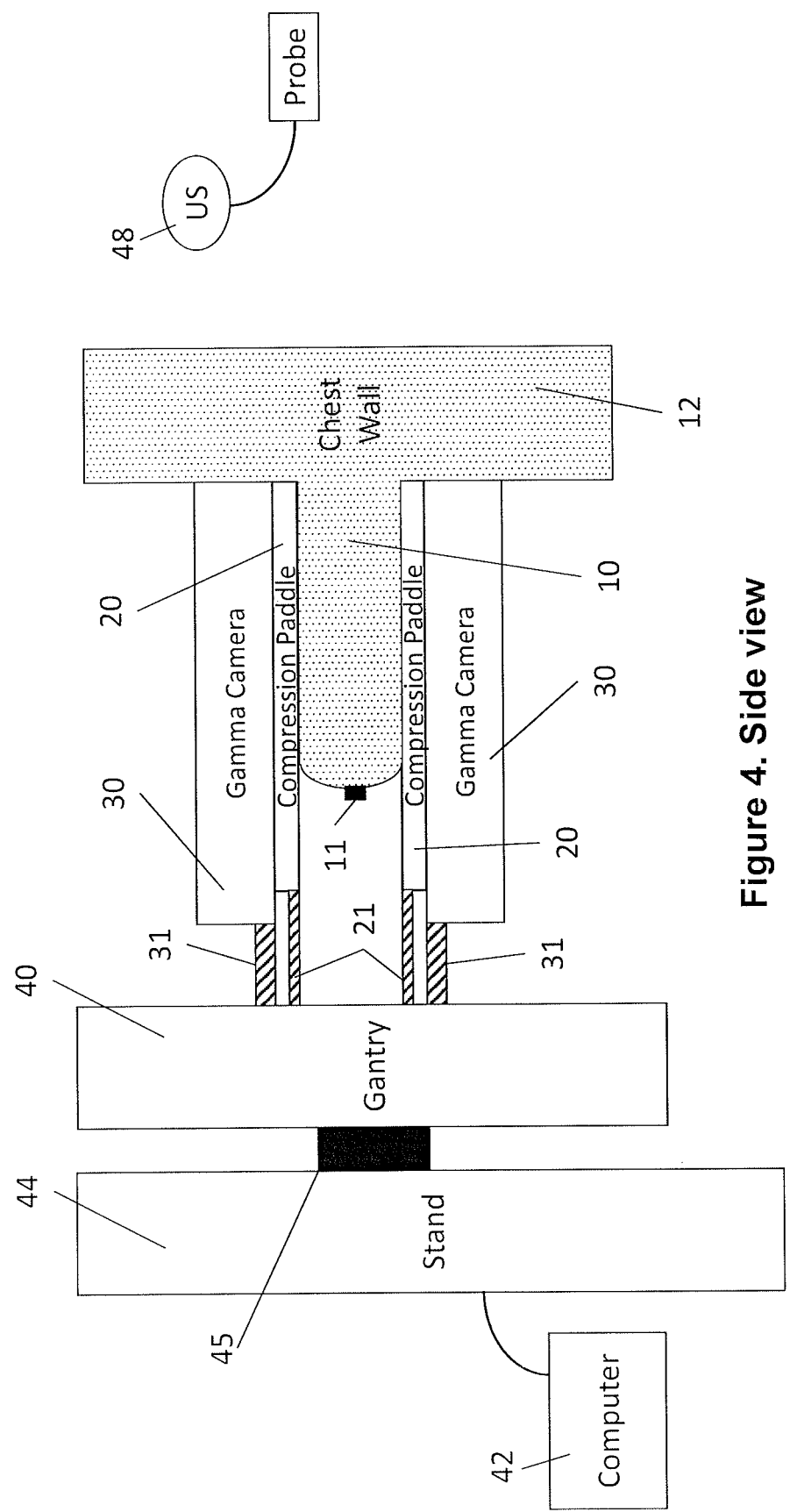
Figure 4. Side view

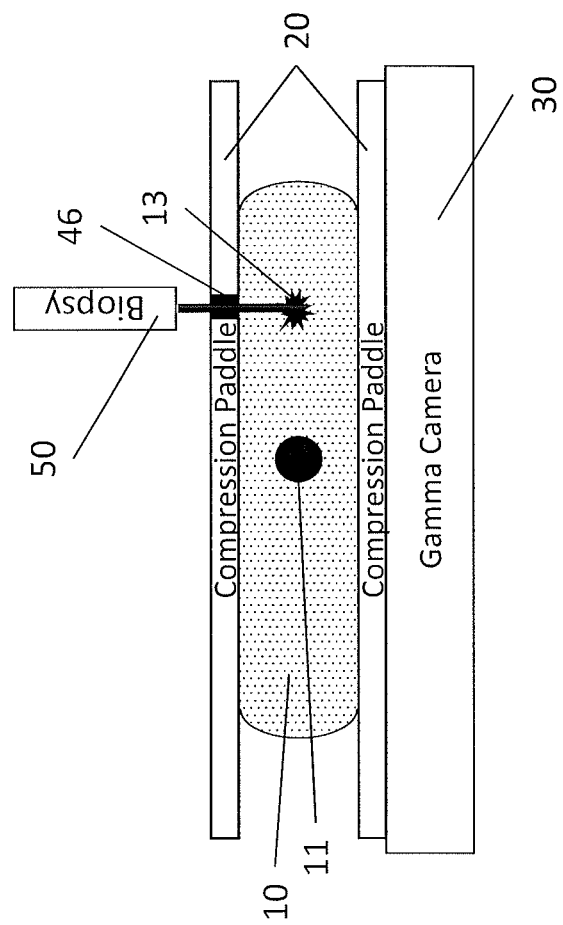
Figure 5. Gantry (Nipple) View - Biopsy

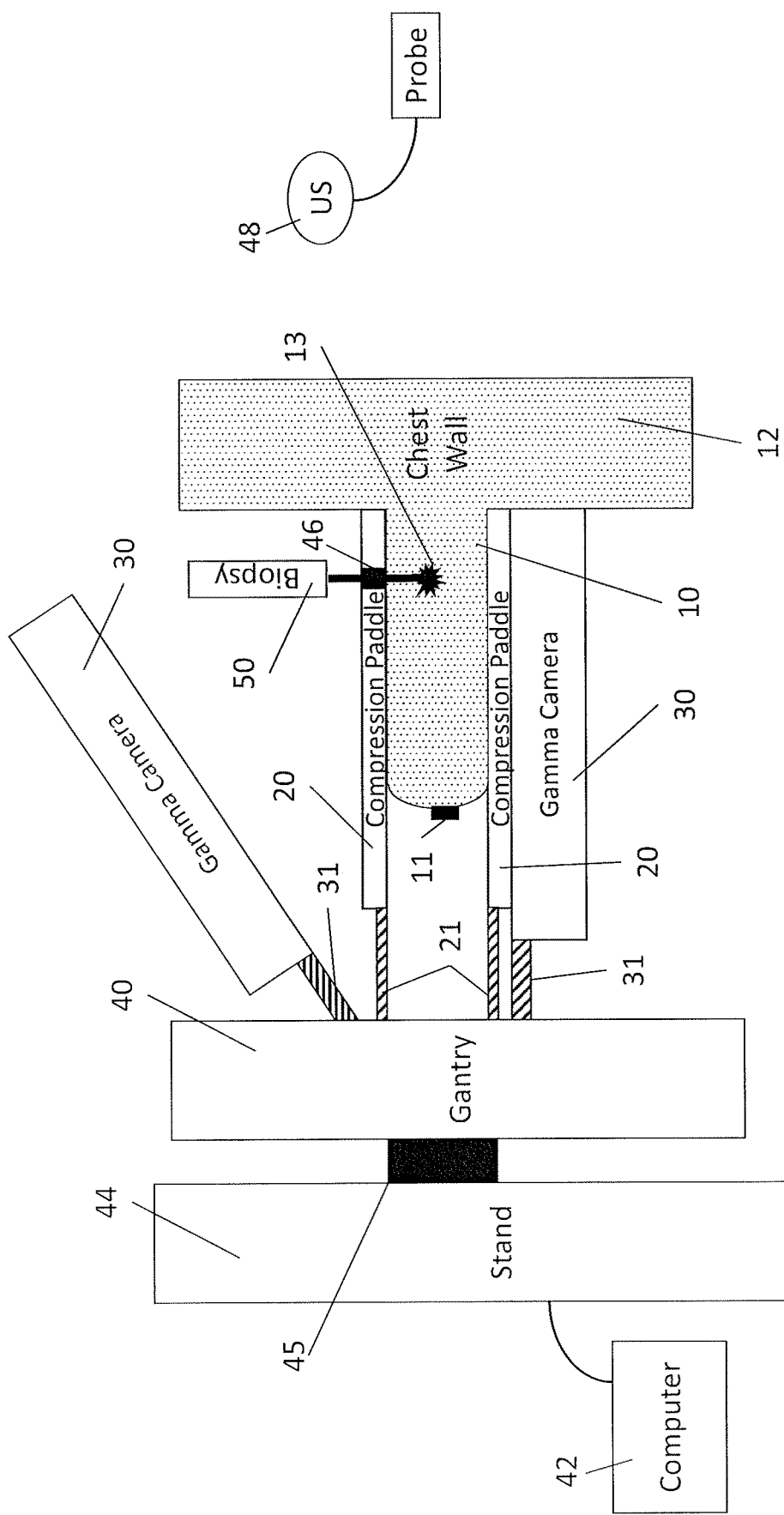
Figure 6. Side View - Biopsy

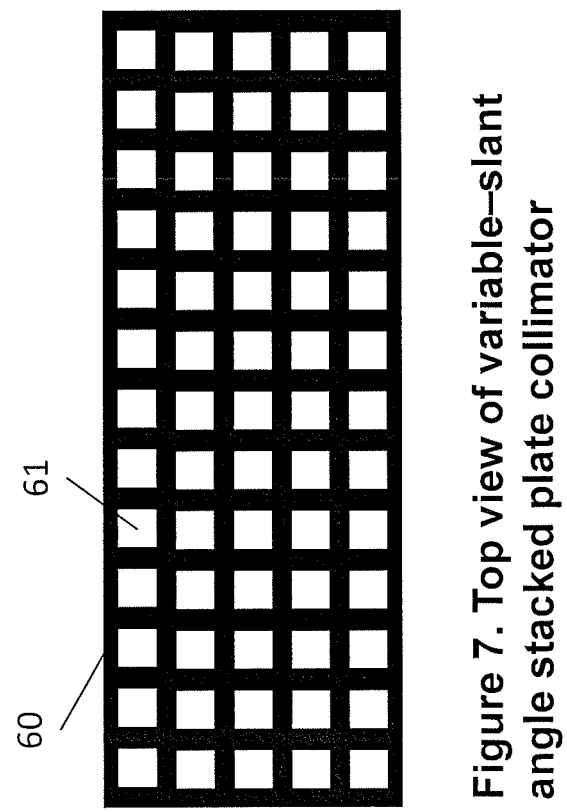
Figure 7. Top view of variable-slant angle stacked plate collimator

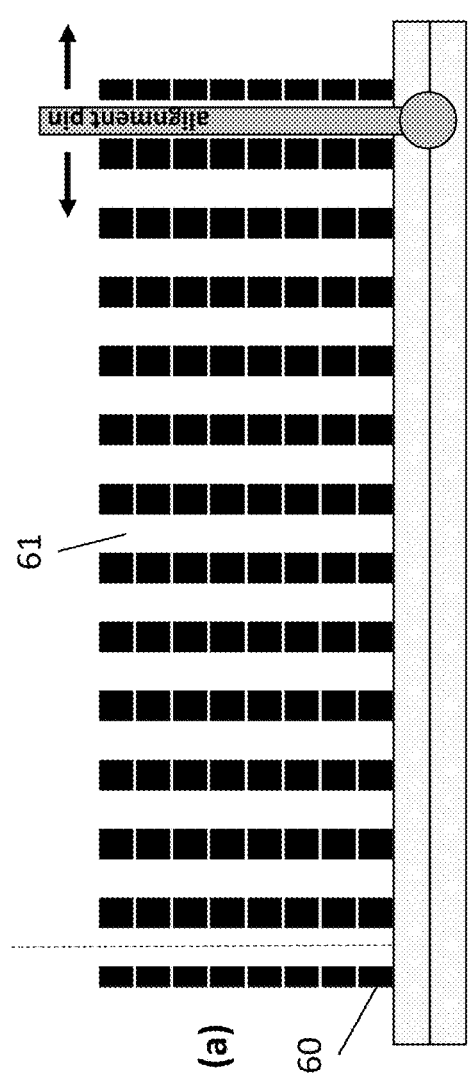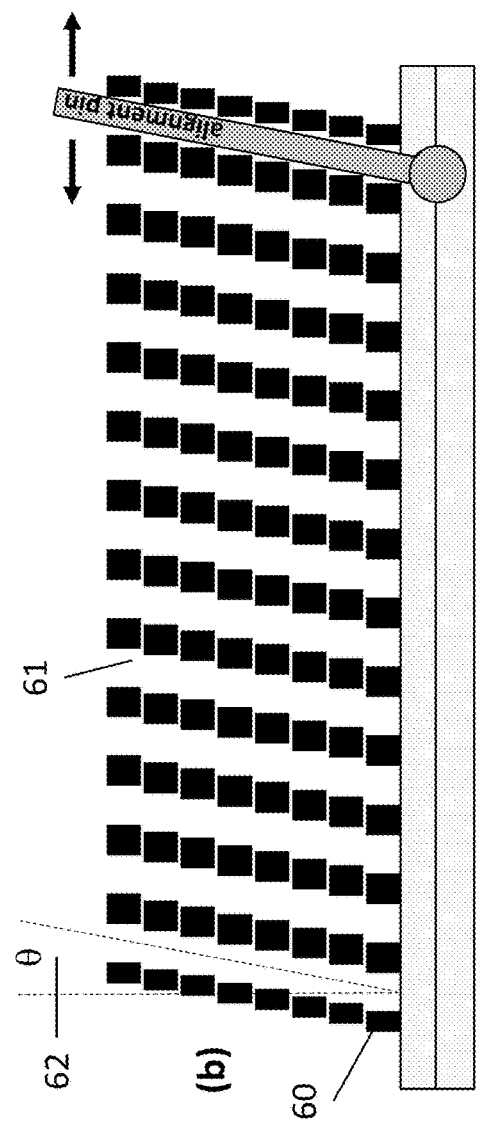
Figure 8. Side view of variable – slant angle stacked plate collimator – side view

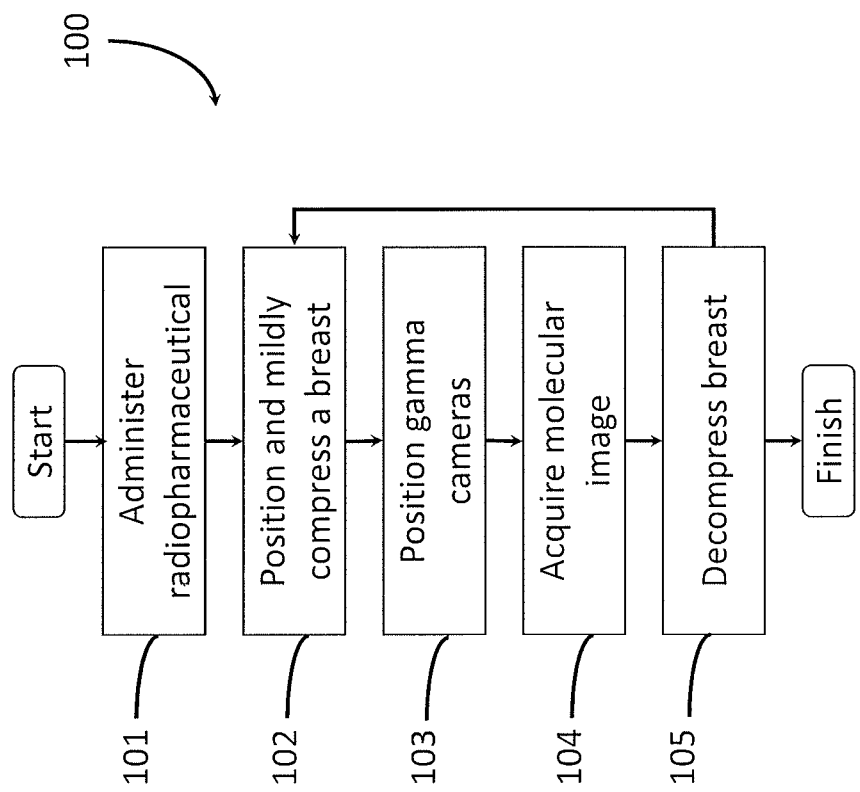
Figure 9. MBI flow chart.

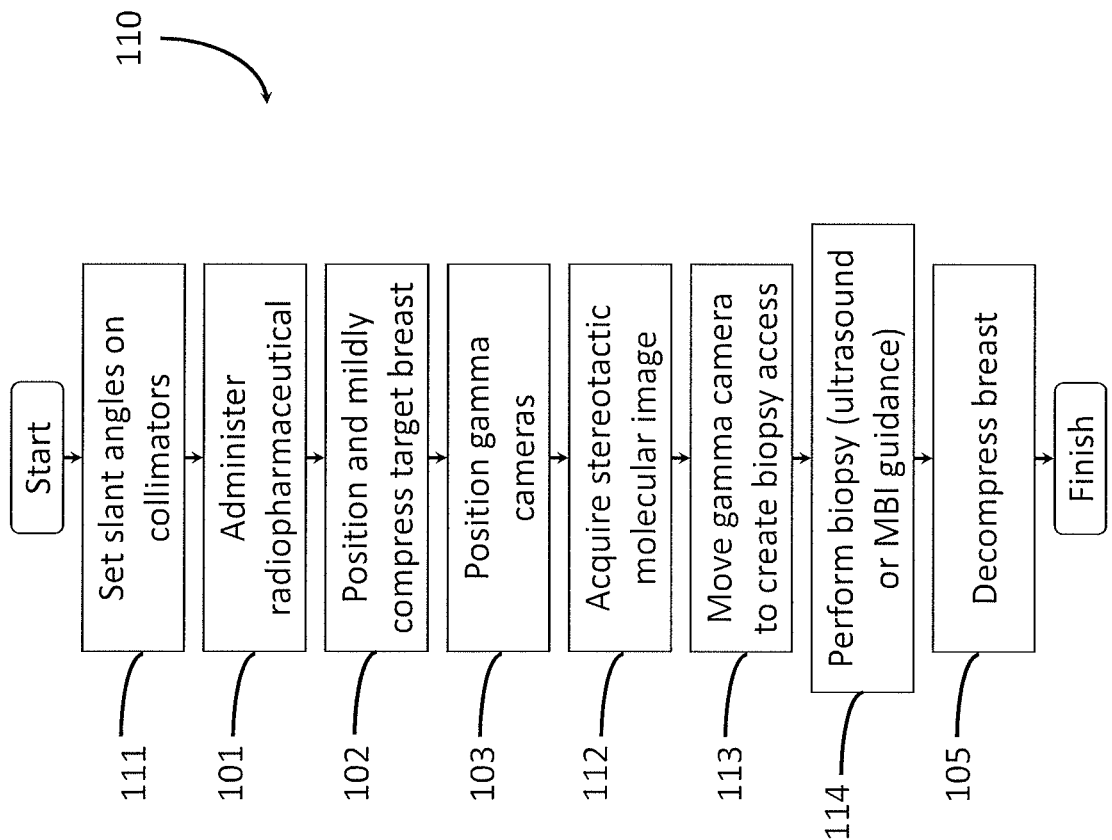
Figure 10. MBI biopsy or surgery guidance flow chart.

MOLECULAR BREAST IMAGING METHOD

CROSS-REFERENCE TO RELATED APPLICATIONS

This application is a divisional application of co-pending U.S. patent application Ser. No. 15/096,075, entitled "Molecular Breast Imaging with Biopsy Guidance", filed Apr. 11, 2016, which claims priority to and benefit of U.S. Provisional Patent Application No. 62/145,790 filed on Apr. 10, 2015, entitled "Gamma Emission Imaging and Tomography with Pixelated Detectors," the contents of which are hereby incorporated by reference in their entirety.

FIELD OF THE INVENTION

The present invention relates to systems and methods for molecular breast imaging (MBI) for cancer detection (screening), diagnosis, image-guided intervention (biopsy, surgery), or therapy monitoring. The medical field of application is Breast Radiography using the principles of Nuclear Medicine (also known as "Molecular Imaging") which image single gamma photon emission following injection of a radioisotope labelled tracer (molecular imaging agent). The emitted gamma photons are imaged by one or more gamma cameras, where a collimator (parallel hole, focusing, or multiple pinhole) is integral to each gamma camera. The present invention provides for a practical and flexible gantry design for Molecular Breast Imaging (MBI) that can also be used for stereotactic MBI-guided biopsy or surgery.

BACKGROUND OF THE INVENTION

X-ray mammography is the standard of care for breast cancer screening, diagnosis, and stereotactic image guided intervention. However, it is ineffective in women with radiographically dense breast tissue, who comprise about half of women over age 40. Recently, "3D mammography" ("tomosynthesis") was introduced to partially alleviate the challenge of dense breast tissue. It enables a small improvement over planar mammography (digital or film), but it still suffers from the fact that cancer and dense tissue look similar on x-ray transmission images. Dense breast tissue is transparent to gamma photon emission, making MBI a potentially superior solution. Several commercial solutions have been offered. Naviscan introduced a PET solution labeled PEM (positron emission mammography), but the cost and dose are too high, reimbursement is a challenge, and a significant fraction of tumors cannot be detected with 18F_FDG. Three companies have introduced single-photon emission MBI products: Dilon Technologies offers a single scintillator camera solution at lowest cost but highest dose; Gamma Medica and General Electric both offer dual CZT (CdZnTe solid-state direct conversion) camera solutions. The cost of the CZT cameras is still high, although the effective dose has been reduced by to be nearly equivalent to screening mammography. Reimbursement for single-photon MBI is better than PET, but it is still challenging. Neither Gamma Medica nor General Electric yet offer a biopsy-guidance solution, which has hindered adoption.

Expired U.S. Pat. No. 5,519,221 (Weinberg, Naviscan) describes a generic MBI apparatus and method (FIG. 1) in which the breast is lightly compressed (painlessly immobilized) by two compression plates (also known as "paddles"). Two gamma cameras, offset by some distance, record multiple image views to be reconstructed into a tomosynthetic image. One of the most significant drawbacks of this design is poor image resolution because of the long distance from the collimator to the breast tissue. U.S. Pat. No. 6,377,838 (Iwanczyk and Patt, Gamma Medica) describes an MBI apparatus and method (FIG. 2) in which the compression paddles are eliminated and the collimators of the two gamma cameras are in direct contact with the breast tissue and thus form an integral part of the compression mechanism. This patent also requires the retrofitted attachment of the MBI gamma cameras to a mammography machine.

U.S. Pat. Nos. 8,217,357 and 8,592,772 (Stein, et al., Hologic) describe an integrated x-ray tomosynthesis and MBI system with sequential imaging by the two modalities. The use of slanted parallel-hole collimators for stereotactic imaging of lesions for biopsy guidance is described as well as several schemes for moving one of a pair of gamma cameras to create access for a biopsy needle. U.S. Pat. Nos. 8,115,171 and 8,541,748 (Blevis, General Electric) describe MBI biopsy guidance using two gamma cameras positioned at an angle (typically 90 degrees) to each other to provide stereotactic imaging of lesions for biopsy guidance. U.S. Pat. No. 8,610,076 (Blevis, General Electric) describes a generic MBI system with pixelated CZT gamma cameras and pixel-registered collimators.

U.S. Pat. Nos. 8,886,293 and 9,060,732 (O'Connor, Mayo Foundation) describe a highly focused collimator for real-time biopsy guidance. While the concept is sound, the embodiment is very challenging and unlikely to be implemented in clinical practice. U.S. Pat. No. 8,853,635 and published application 2016/0,007,944 (O'Connor, Mayo Foundation) describe a dual-modality ultrasound and MBI system where biopsy guidance is provided by ultrasound.

BRIEF SUMMARY OF THE INVENTION

This invention addresses several problems of current commercial solutions and prior patents, for examples: 1) in current dual-camera MBI systems the technologist cannot see the breast to properly position it while applying mild compression; 2) in current dual-camera MBI systems a biopsy cannot be easily performed because the biopsy device can only be introduced from the side between the two cameras; 3) in current dual-camera MBI systems no accurate depth of lesion information is available with standard parallel-hole collimation; 4) in current MBI systems, the chest wall is not imaged, so lesions can be missed; 5) a single camera MBI system is only half as efficient as a dual-camera system, so dose or exam time must be increased and lesions on the distal side of the breast may be missed; 6) in current MBI systems the collimators must be exchanged to alter their performance characteristics, such as slant-hole angle; 7) in current MBI systems the cameras are flat, but breasts are curved; 8) in current MBI systems only a few (typically two) planar projection images are acquired; 9) in current MBI systems, the compressive force can vary significantly with the view angle.

This invention provides a system for performing MBI with optional biopsy or surgery guidance. The system comprises a stand with a rotatable gantry, two compression paddles and two gamma cameras with collimators connected to the gantry, and a computer with software to control system motions and acquire MBI images. One or both gamma cameras can be moved away from the breast to enable access for core needle biopsy or other surgical procedure through one or more apertures in one or both compression paddles. In one embodiment, a hand-held ultrasound probe can guide the biopsy or surgery through an aperture in one of the compression paddles. The collimators in one embodiment have a pixel-registered slant-hole configuration. In another embodiment, the collimators have a variable-angle pixel-registered slant-hole configuration.

This invention provides a method for performing MBI using the disclosed system. The method comprises administering a radiopharmaceutical, positioning a breast and mildly compressing it, moving the gamma cameras into position, acquiring a molecular image, decompressing the breast, and repeating the positioning through imaging steps for each clinical view desired. Typically, both CC (cranial-caudal) and MLO (medio-lateral oblique) views are acquired for both the left and right breasts.

This invention further provides a method for performing MBI for biopsy or surgery guidance. Assuming that a previous MBI has been performed and a suspect lesion has been identified, a single view is planned to provide the best access to the lesion. The variable-angle pixel-registered slant-hole collimator is used, if available. The method comprises setting the slant angles according to plan, administering a radiopharmaceutical, positioning the target breast and mildly compressing it, moving the gamma cameras into position, acquiring a stereotactic molecular image, moving a gamma camera to create access, performing biopsy or surgery under either ultrasound or MBI guidance, and decompressing the breast to finish the procedure.

BRIEF DESCRIPTION OF THE DRAWINGS

The organization and manner of the structure and operation of this invention, together with further objects and advantages thereof, may best be understood by reference to the following description, taken in connection with the accompanying non-scale drawings, wherein like reference numerals identify like elements in which:

FIG. 3 is a gantry (nipple) view of the device of the preferred embodiment of the present invention.

FIG. 4 is a side view of the device of FIG. 3.

FIG. 5 is a gantry (nipple) view of the device of FIG. 3 in biopsy or surgery guidance mode.

FIG. 6 is a side view of the device of FIG. 3 in biopsy or surgery guidance mode.

FIG. 7 is a top view of the variable-slant angle stacked-plate collimator core of an embodiment of the invention.

FIG. 8 is a side view of the variable-slant angle stacked-plate collimator core of an embodiment of the invention.

FIG. 9 is a flow chart of a method for performing MBI according to an embodiment of the invention.

FIG. 10 is a flow chart of a method for performing MBI biopsy or surgery guidance according to an embodiment of the invention.

DETAILED DESCRIPTION OF THE ILLUSTRATED EMBODIMENTS

Figure 1:
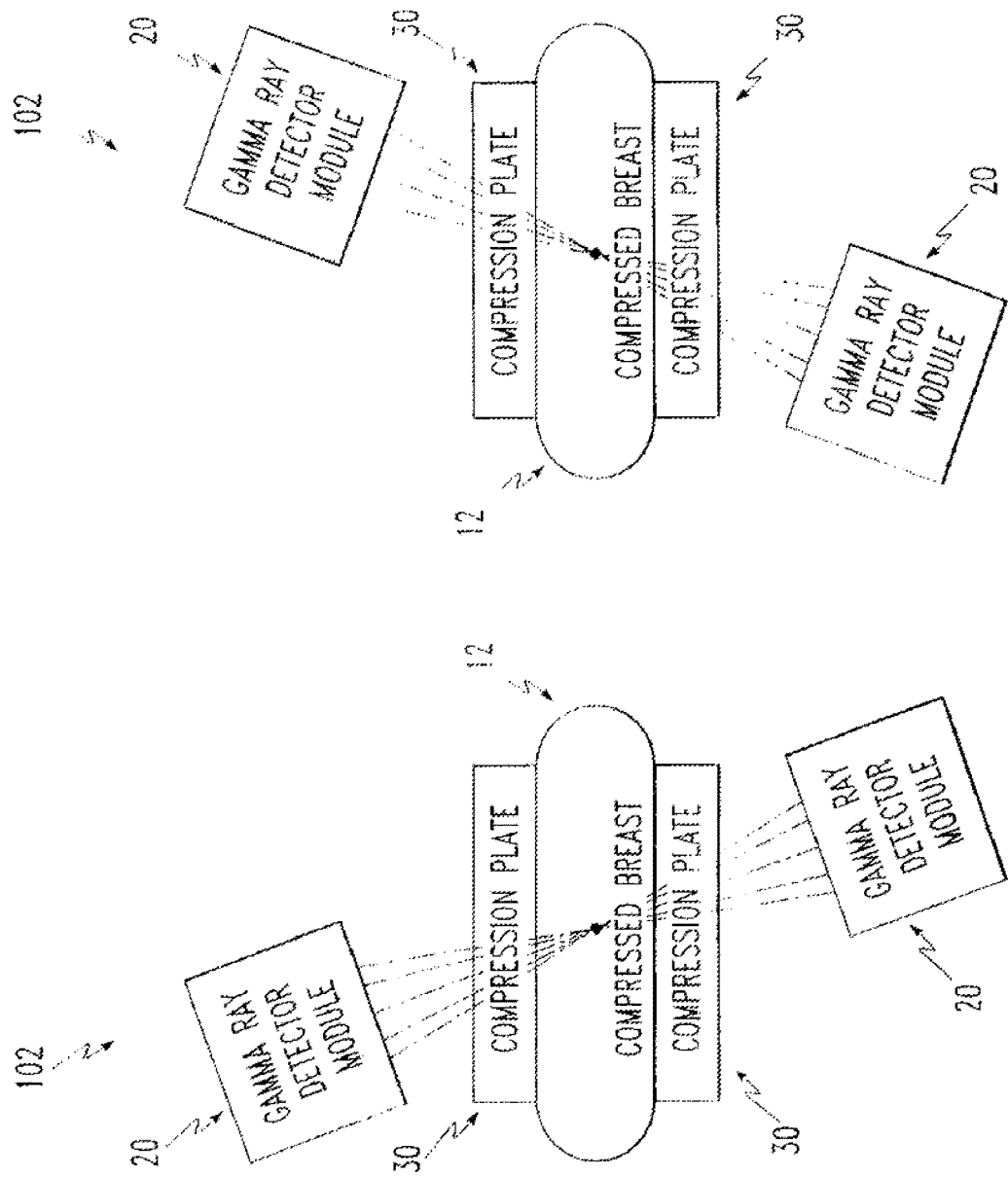
FIG. 1 is a molecular breast imaging system as known in the prior art.
Figure 2:
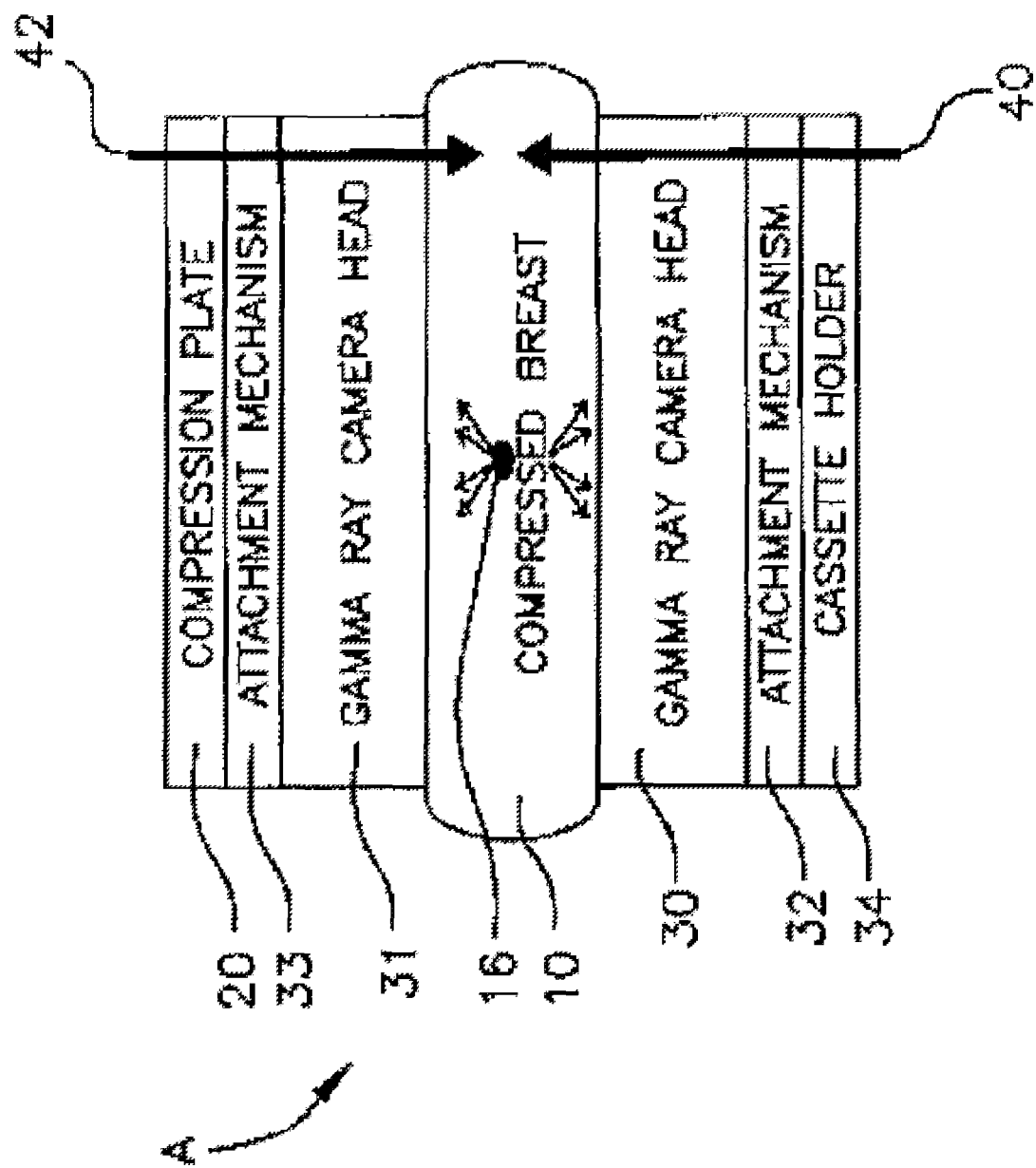
FIG. 2 is another molecular breast imaging system as known in the prior art.

While the invention may be subject to embodiment in different forms, there is shown in the drawings, and herein will be described in detail, specific embodiments with the understanding that the present disclosure is to be considered an exemplification of the principles of the invention, and is not intended to limit the invention to that as illustrated and described herein.

FIGS. 3 and 4 illustrate a preferred embodiment of the invention in its MBI imaging mode for the mildly compressed breast (10). FIG. 3 shows the system from the viewpoint of the gantry (40) looking toward the patient with the nipple (11) visible. FIG. 4 is a side view with the gantry (40) on the left and the patient's chest wall (12) on the right with breast (10) and nipple (11) positioned toward the gantry (40). Thin compression paddles (20), preferably transparent plastic such as acrylic, directly contact and immobilize the breast (10). Two gamma cameras (30) are positioned in contact with the compression paddles (20), but they do not contribute to the compression. Those skilled in the art will appreciate that a computer (42) with software will preferably control motions of the gantry (40), gamma cameras (30), and compression paddles (20) as well as acquire, process, and display the gamma emission images collected during the MBI examination. Alternatively, manual control can be used to adjust the positions of the gantry (40), gamma cameras (30), and compression paddles (20) and to control the cameras (30).

It is understood that the gantry assembly consists of the gantry (40) which supports the compression paddles (20) and gamma cameras (30) and which is rotatably connected by a rotor (45) to a stand (44) which supports the weight of the gantry assembly and provides power and data transmission between the gamma cameras (30) and the computer (42).

The preferred embodiment employs two gamma cameras, but a single camera can be used to reduce system cost at the expense of higher dose or longer exam time (as in the current commercial offering from Dilon). Alternatives with more than two small cameras can be envisioned in the spirit of the invention.

As those skilled in the art will understand, the gamma cameras (30) comprise a collimator and a detector assembly. In a preferred embodiment, the collimator may have a pixel-registered square parallel-hole core and the detector assembly may be an array of pixelated CZT detectors. The collimator can comprise parallel-hole, slant-hole, focusing (convergent or divergent), multiple-pinhole collimators, or Compton camera (a form of "electronic collimation"). For pixelated detectors, pixel-registered square-hole collimators are preferred, but traditional hexagonal-hole collimators can also be used (although they are not as efficient). Alternatively, the detector assembly may comprise a scintillator (pixelated or monolithic) and an array of photodetectors, such as vacuum photomultiplier tubes (PMTs), position-sensitive PMTs-PSPMTs, avalanche photodiodes (APDs), or solid-state photomultipliers (also called silicon photomultipliers or SiPMs).

The compression paddles (20) are preferably transparent (plastic), although they could be made of thin carbon fiber. There can be multiple varieties of compression paddles (as in mammography), some solid and some with apertures of various sizes for biopsy or surgery access. The compression paddles (20) are not required to be planar. They may be curved (concave) to better conform to the shape of the breast (10). The gamma cameras (30) can also be curved, especially when composed of modular pixelated detectors, to fit the curvature of the compression paddles (20).

The paddles (20) and gamma cameras (30) are each mechanically attached by separate support arms (21 and 31, respectively) to the MBI gantry. The compression paddles (20) are mechanically independent of the gamma cameras (30). The compression paddle support arms (21) are directly connected to the gantry (40). The gamma camera support arms (31) are able to position the gamma cameras (30) in direct contact with the thin compression paddles (20) so that the gamma cameras (30) are as close as possible to the breast (10), which will optimize the image quality as will be apparent to those skilled in the art. However, the gamma cameras (30) do not directly contact the breast (10) and do not provide any compressive force on the breast (10) as in U.S. Pat. No. 6,377,838 (Iwanczyk and Patt, Gamma Medica). As will be apparent to those skilled in the art, this invention places the gamma cameras (30) further away from the breast (10), typically by a fraction of a centimeter, thus at a slight disadvantage with respect to U.S. Pat. No. 6,377,838, but with significant advantages in clinical practice. The typical design of a compression paddle (20), as is well-known by those skilled in the art, is similar in geometry to a cut-away of the bottom of a box. That is, there is a bottom surface that contacts the breast (10) and there are four sides to give mechanical strength to the paddle. These four sides and bottom constitute a "well" into which the gamma camera (30) can be designed to fit loosely. The compression paddle (20) is connected by at least two support arms (21) to the compression mechanism of the gantry (40).

The gamma camera support arms (31) are articulated to tilt, rotate, or otherwise move one or both of the gamma cameras (30) out of the immediate vicinity of the breast (10) when not imaging. This ability to move a gamma camera (30) out of the way, while keeping the breast (10) immobilized by the compression paddles (20) provides an advantage during the positioning of the breast (10) prior to imaging and also during biopsy or surgery guidance, as will be illustrated next.

FIGS. 5 and 6 illustrate a preferred embodiment of the invention in its MBI biopsy or surgery guidance mode for the mildly compressed breast (10). FIG. 5 shows the same gantry (40) or nipple (11) perspective as FIG. 3 while FIG. 6 shows the same side view perspective of FIG. 4. By way of illustration, the top gamma camera (30) is tilted away from the breast (10), exposing the top compression paddle (20), which may have an aperture (46) (typically 10 cm×10 cm). The compression paddle (20) may optionally have a grid of smaller apertures (46) (not shown, but typically on a 1-cm pitch) through which a core biopsy needle (50) can be introduced to sample an imaged lesion (13).

FIG. 6 shows the top gamma camera (30) tilted away with a pivot point hidden inside the gantry (40). This is a preferred embodiment, but other motions are also contemplated. One optional movement would be to slide the gamma camera (30) toward the gantry (40) using the support arms (31) as rails. One or more apertures (46) in the compression paddle (20) could thus be exposed for access by a biopsy core needle (50). Another possible motion is to rotate the gamma camera (30) about the vertical axis of the gantry (40) to expose the compression paddle (20). Those skilled in the art can understand that similar motions that expose the breast (10) for biopsy or surgery access are anticipated by this invention.

Alternatively, an ultrasound probe (48) can be used in the compression paddle (20) aperture to guide a biopsy needle (50), since about 85% or more of lesions seen by MBI can also be seen on ultrasound. The very high specificity of MBI is thus used to select lesions for biopsy or surgery. Ultrasound, which is sensitive to detect lesions has a low specificity for selecting lesions likely to be malignant. So ultrasound alone is not an ideal screening tool, but paired with MBI for lesion detection, ultrasound is a very effective tool for biopsy or surgery guidance. This invention differs from U.S. Pat. No. 8,853,635 and application 2016/0007944 (O'Connor, Mayo Foundation) in that only a small aperture (46) in the compression paddle (20) is required to provide access for a small hand-held ultrasound probe (not shown) and a core biopsy needle (50).

The MBI gantry (40) has several additional degrees of freedom of motion in addition to those already described: axial motion of the compression paddles (20) along the axis between the two paddles to provide immobilization of the breast (10); axial motion of the gamma cameras (30) to bring them into direct contact with the compression paddles; tilt, rotation, or translation of the gamma cameras (30) away from the breast to move them out of the way for breast (10) positioning or biopsy or surgery guidance. In addition, the whole gantry assembly comprising the two compression paddles (20) and two gamma cameras (30) can rotate around the rotor (45) which is at the isocenter of the assembly (which is approximately the axis from the nipple (11) to the chest wall (12)) to support different views of a breast, similar to mammography. For example, the CC (cranial-caudal) view is along an axis roughly parallel to the patient's long axis and the MLO (medial lateral oblique) view is approximately 40 to 60 degrees rotated with respect to the CC view so that the pectoral muscle can be included in the cameras' field of view. Further, the whole assembly must be able to move vertically, that is, to adjust the height from the floor to match the patient's breast (10) position. Generally, for screening or diagnostic MBI, the patient will be sitting or standing. But for biopsy or surgery guidance, it may be more convenient for the patient to lie on her contralateral side (lateral decubitus) to the breast (10) to be biopsied, which will be more accessible on top.

Note that when the compression paddle (20)/gamma camera (30) assembly rotates to different angles with the vertical, the compressive force must be adjusted to compensate for the vertical force of gravity. To enable this adjustment automatically (for example, by a table lookup or a microcontroller calculation), it may be useful to include a tilt-meter in the assembly or to have an angular encoder for the rotation.

FIGS. 7 and 8 show a collimator invention that can be utilized in normal MBI mode for screening or diagnostic imaging, as well as assist in stereotactic biopsy or surgery guidance. In the three commercial single-gamma-photon MBI systems, the gamma camera is pixelated (Dilon uses 3.2 mm square CsI pixels; GE uses 2.5 mm pitch square CZT pixels; Gamma Medica uses 1.6 mm pitch square CZT pixels). All three use a pixel-registered square parallel-hole collimator matched with one hole per pixel. Dilon also uses a slideable slant-hole collimator for biopsy guidance, requiring two separate images for stereotactic lesion location.

One preferred embodiment of the present invention is to provide stereotactic lesion location by using a pixel registered square slant-hole collimator on both gamma cameras. A 15-30 degree slant on each is sufficient for lesion triangulation. Preferably, the collimator holes would slant inwards toward the chest wall to provide the extra benefit of imaging the chest wall tissue. Of course, as those skilled in the art are aware, the heart and liver must not appear in the breast image to avoid overwhelming the gamma emission from breast. These pixel-registered square slant-hole collimators could be permanently integrated with the gamma cameras (30).

FIGS. 7 and 8 show how a variable angle slant-hole collimator can be constructed by stacking planar layers of grids (such as etched tungsten) and linearly varying the offset between layers. FIG. 7 shows a top view of the collimator core comprising a plurality of plates, each with metal septa (60) and an array of square holes (61). Only a small portion of a clinically sized collimator core is illustrated here. FIG. 8 shows side views of a small portion of the variable-slant angle stacked plate collimator in two potential positions. In FIG. 8 (a), the stack of collimator plates is shown with zero slant angle as shown by the vertical dashed line overlaid on the leftmost column of aligned square holes, thus forming a typical parallel-hole collimator that admits gamma photons travelling essentially perpendicular to the detector entrance surface, that is, with normal incidence. In FIG. 8 (b), an angle theta (8, 62) describes the slant of the collimator holes with respect to normal incidence. A lubricant (e.g., graphite or oil) may be needed to allow smooth gliding of the metal plate layers. Alignment pins connecting all layers may be slanted like a joystick to change the slant angle. The slant may be controlled manually or automatically by use of motors or actuators. The collimator slant angle (62) may be adjusted specifically for each patient to accommodate anatomical and body habitus variations. In particular, the technologist will want to avoid exposing the gamma cameras (30) to direct view of internal organs, such as the heart and liver, which may take up significant concentrations of the radiopharmaceutical.

FIG. 9 is a flow chart (100) illustrating the essential steps in the acquisition of an MBI examination using the system described above. Patients for MBI are typically required to remove their top outer clothing and brassiere and to dress in a gown that provides easy access to either breast (10). The first step (101) of the examination is to administer the radiopharmaceutical to the patient, which is typically a venous injection of $^{99m}$Tc-sestamibi or, in Europe, $^{99m}$Tc-_tetrafosmin. Both radiopharmaceuticals were initially indicated for myocardial perfusion imaging (MPI), but they have also proven to have avid uptake in breast tumors with a typical concentration in tumors of 20 times the background parenchymal uptake. The uptake is rapid and imaging can begin within 5 minutes or less after the injection. In some imaging centers, the injection is performed in the Nuclear Medicine department and the imaging is performed in the Breast Radiology department. In other centers, the breast radiology technologists have been trained and certified to inject radiopharmaceuticals. In very few centers, the entire examination is performed in the nuclear Medicine department, where access to breast patients is challenging.

The next step (102) is to position and mildly compress a breast. One advantage of this invention is that ether gamma camera (30) can be moved away from the breast (10) to expose the transparent compression paddles (20) which facilitates positioning of the breast and application of mild compression. The third step (103) is to position the gamma cameras that were moved away at the start of the exam. As noted above, the gamma cameras (30) can be designed to fit loosely within the "well" of the compression paddles (20), in direct contact with the bottom surface of the paddles (20), but not contributing any compressive force. After this step, the system is set up for the fourth step (104) to acquire a molecular image. In most commercial systems, the time to acquire MBI images ranges from five to ten minutes per view and four views are typically acquired: CC and MLO positions for both left and right breasts. The fifth step (105) is to decompress the breast (10) and repeat the second step (102) through the fifth step (105) until all views have been acquired. After the last decompression, the examination is finished and the patient can redress in street clothes.

FIG. 10 is a flow chart (110) showing a variation on the method of FIG. 9 appropriate for biopsy or surgery guidance. We assume that a previous MBI for the patient has identified one or more suspicious lesions that require biopsy or surgery. The biopsy could occur the same day as a screening or secondary diagnostic exam with MBI. Before the examination begins, the slant angles of the variable angle collimator can be set (111). The next three steps (101, 102, and 103) are the same as in an MBI imaging examination. Typically, the breast radiologist will order a higher dose of radiopharmaceutical for a biopsy to improve the image quality and shorten the image acquisition time. The perceived risk of a higher dose is mitigated by the potential benefit of detecting cancer earlier when it is more treatable. The other difference is that a single view can be planned in advance to give the best access by the biopsy core needle (50) or surgical tools to the suspect lesion (13). The next step (112) is to acquire a stereotactic molecular image of the suspect lesion. After simple triangulation, the three-dimensional location of the lesion (13) will be known, typically within several millimeters.

The next step (113) is to move a gamma camera (30) to create biopsy access by tilting (as in FIG. 6, a preferred embodiment), rotating, or translating the camera (30) away from the breast (10). The next step (114) is to perform the biopsy or surgery under ultrasound or MBI guidance. Ultrasound guidance is fast and reimbursable. It should be preferred in the about 85% of cases where ultrasound is able to visualize the same lesion identified by MBI. In the remainder of cases, MBI can be used to guide the biopsy. Briefly, after a trocar is placed into the three dimensional lesion location (13) determined by the stereotactic MBI (113), a line source containing $^{99m}$Tc or $^{57}$Co can be placed in a sleeve (disposable or sterilizable) and inserted into the trocar to the tip. Another MBI image can be acquired to confirm the trocar positioning with respect to the target lesion (13). The line source can be retracted and one or more core biopsy samples extracted. The samples can be imaged by the gamma cameras (30) to verify that they contain a high concentration of the radiopharmaceutical and to visualize the margins. Finally, after completing the biopsy or surgery and closing the wound, the breast can be decompressed (105) and the procedure is finished. Although this description of an MBI-guided biopsy is brief, it illustrates the essential elements.

New features of this invention include 1) tiltable (or rotatable or translatable) gamma cameras for breast positioning and biopsy or surgery guidance, 2) variable angle slant-hole collimator, 3) curved compression paddles with curved gamma cameras (from tiled pixelated detector modules), and 4) use of camera assembly angle to adjust compressive force.

The technician is better able to position the breast by viewing it through the transparent compression paddles before the gamma cameras are positioned for imaging. This is an advantage over the Gamma Medica and General Electric commercial systems. As a further advantage over U.S. Pat. No. 6,377,838 (Iwanczyk and Patt, Gamma Medica), the MBI cameras are explicitly not attached to a mammography machine, but have an independent MBI dedicated gantry.

As an advantage over U.S. Pat. No. 5,519,221 (Weinberg, Naviscan), the gamma cameras (30) are as close as possible to the compression paddles (20), which improves the spatial resolution. However, the cameras are not quite as close as in Iwanczyk and Patt. The small loss in spatial resolution due to the extra distance (thickness of a compression paddle (20)) between the cameras (30) and any lesion (13) in the breast (10) is clinically insignificant.

The ability to perform an MBI-guided biopsy or surgery without moving the breast immediately after detecting a lesion is an advantage over both prior art patents and over all current commercial MBI systems.

One advantage of the variable-angle slant-hole collimator design (FIGS. 7 and 8) is that either parallel-hole or slant-hole imaging may be performed without swapping collimators. Also, during biopsy or surgery guidance, when one of the cameras (30, and its collimator) is tilted (or rotated or translated) away from the breast (10), the remaining camera (30) can still stereotactically verify the lesion and biopsy needle position by acquiring two images with the slant-hole collimator set at plus and then minus 15 degrees, for example.

Use of the camera assembly angle to adjust the compressive force will assure more consistent imaging results (same compression in all views) and will provide safety for consistent compressive force limits, regardless of the direction of gravity.

While preferred embodiments of the present invention are shown and described, it is envisioned that those skilled in the art may devise various modifications of the present invention without departing from the spirit and scope of the appended claims.

What is claimed is:

1. A molecular imaging method for imaging a breast of a patient, the method comprising:
    administering a radiopharmaceutical to the patient;
    positioning a molecular imaging system, the system comprising:
        a stand;
        a gantry connected to and movable in relation to the stand;
        a first support arm articulated to the gantry;
        a first gamma camera connected to the first support arm;
        a second support arm articulated to the gantry;
        a second gamma camera connected to the second support arm;
        a third support arm articulated to the gantry;
        a first compression paddle connected to the third support arm;
        a fourth support arm articulated to the gantry;
        a second compression paddle connected to the fourth support arm;
        wherein the first support arm, the second support arm, the third support arm, and the fourth support arm are each mechanically independent and configured to be articulated independently relative to the gantry;
        wherein the first gamma camera, the second gamma camera, the first compression paddle, and the second compression paddle are each mechanically independent;
        at least one pixel-registered collimator with slant holes; and
        a controller connected to the gantry to control movements of the gantry, movements of the support arms, and an acquisition of an image by at least one of the cameras;
    positioning and compressing the breast utilizing the first compression paddle and the second compression paddle;
    positioning the slant holes of the at least one pixel-registered collimator towards a chest wall tissue;
    acquiring a molecular image; and
    decompressing the breast.

2. The method of claim 1, wherein at least one of the first compression paddle and
the second compression paddle comprises an aperture and the method further comprises a step comprising at least one of a biopsy and a surgical procedure.

3. The method of claim 1, wherein the molecular imaging system further comprises an ultrasound probe.

4. The method of claim 1, wherein at least one of the first compression paddle and the second compression paddle comprises a concave curved surface.

5. The method of claim 1, wherein the at least one pixel-registered collimator with slant holes comprises a variable-angle slant-hole collimator comprising a plurality of slidable stacked plates and one or more slantable alignment pins, the plates comprising an array of pixel registered holes.

6. The method of claim 1, wherein at least one of the first gamma camera and the second gamma camera comprises the at least one pixel-registered collimator and a detector assembly.

7. The method of claim 6, wherein the other of the first gamma camera and the second gamma camera comprises at least one of a parallel-hole collimator, a slant-hole collimator, a focusing collimator, and a multiple-pinhole collimator.

8. The method of claim 6, wherein the gantry has an axis and at least one of the support arms is at least one of translatable parallel to the axis, rotatable to the axis, translatable radially to the axis, and tiltable with respect to the axis.

9. The method of claim 6, wherein the detector assembly comprises a scintillator and an array of photodetectors.

10. The method of claim 6, wherein the detector assembly comprises an array of solid-state detectors.

* * * * *